US006423029B1

(12) United States Patent
Elsberry

(10) Patent No.: US 6,423,029 B1
(45) Date of Patent: Jul. 23, 2002

(54) SYSTEM AND METHOD FOR DETECTING ABNORMAL MEDICAMENT PUMP FLUID PRESSURE

(75) Inventor: Dennis D. Elsberry, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/301,935

(22) Filed: Apr. 29, 1999

(51) Int. Cl.[7] ............................................. A61M 31/00
(52) U.S. Cl. ...................................................... 604/65
(58) Field of Search ........................... 604/131, 65, 66, 604/67, 151, 153, 246, 132, 133

(56) References Cited

U.S. PATENT DOCUMENTS

| | | | |
|---|---|---|---|
| 4,244,365 A | | 1/1981 | McGill et al. ............... 128/214 |
| 4,256,437 A | | 3/1981 | Brown ........................ 417/45 |
| 4,373,525 A | | 2/1983 | Kobayashi .................. 128/214 |
| 4,468,219 A | | 8/1984 | George et al. ................ 604/66 |
| 4,576,556 A | | 3/1986 | Thompson .................. 417/477 |
| 4,690,673 A | | 9/1987 | Bloomquist .................. 604/67 |
| 4,692,147 A | | 9/1987 | Duggan ........................ 604/93 |
| 5,096,385 A | * | 3/1992 | Georgi et al. ................ 417/18 |
| 5,103,211 A | * | 4/1992 | Daoud et al. ............... 340/608 |
| 5,293,879 A | | 3/1994 | Vonk et al. ................. 128/782 |
| 5,695,473 A | * | 12/1997 | Olsen .......................... 604/153 |
| 5,711,316 A | | 1/1998 | Elsberry et al. ............. 128/898 |
| 5,814,014 A | | 9/1998 | Elsberry et al. .............. 604/43 |
| 5,827,223 A | * | 10/1998 | Butterfield ................... 604/65 |
| 5,832,932 A | | 11/1998 | Elsberry et al. ............. 128/898 |

* cited by examiner

Primary Examiner—Brian L. Casler
Assistant Examiner—Ann Y. Lam
(74) Attorney, Agent, or Firm—Banner & Witcoff, Ltd.

(57) ABSTRACT

A system is disclosed for providing an indication of abnormal upstream fluid pressure, abnormal downstream fluid pressure, and/or abnormal differential upstream versus downstream fluid pressures for a medicament pump that is implantable within a person's body and has a pressurized source of fluid. The system includes upstream and downstream fluid pressure sensors, which could be commercially available strain gauges attached to, or incorporated into, the wall of the inlet tubing and the wall of the outlet tubing, respectively, for sensing the amount of deformation of the tubing walls as a result of fluid pressure changes. Fluid source overpressurization could be indicated, via activation of an alarm, based upon detection of either: abnormally high upstream fluid pressure; or the difference between the upstream fluid pressure and the downstream fluid pressure exceeding a predetermined range of acceptable values. Pump outlet tube occlusion could be indicated, via activation of an alarm, based upon detection of either: abnormally high downstream fluid pressure; or the difference between the upstream fluid pressure and the downstream fluid pressure being less than a predetermined range of acceptable values. Even when the differential pressure is within an acceptable range of values, the inlet and outlet pressure values can be used to distinguish between (1) normal conditions at both the inlet and outlet; and (2) abnormal conditions at both the inlet and outlet that can not be detected differentially, such as simultaneous overpressurization at both the inlet and outlet.

28 Claims, 6 Drawing Sheets

FIG. 5

| Scenario Number | Inlet Pressure Representation | Outlet Pressure Representation | Difference Pressure Representation | Potentially Abnormal Pressure Detection State |
|---|---|---|---|---|
| 1 | >8.0 | don't care | don't care | source overpressurization |
| 2 | <6.0 | don't care | don't care | Source underpressurization |
| 3 | don't care | >4.0 | don't care | downstream catheter overpressurization/ occlusion |
| 4 | don't care | <2.0 | don't care | downstream catheter underpressurization |
| 5 | 8.0 | 3.0 | 5.0 | normal pressure difference |
| 6 | 7.0 | 3.0 | 4.0 | normal pressure difference |
| 7 | 6.0 | 3.0 | 3.0 | normal pressure difference |
| 8 | 6.0 | 4.0 | 2.0 | downstream catheter occlusion |
| 9 | 8.0 | 2.0 | 6.0 | source overpressurization |

FIG. 6

| CONDITIONS | State | SOURCE PSIA | State | OUTPUT PSIA | DIFFERENTIAL PSID |
|---|---|---|---|---|---|
| Nominal (Sea Level) | No | 18.2 | No | 18.2 | 0 |
| | Yes | 20.2 | No | 18.2 | 2 |
| | Yes | 20.2 | Yes | 20.2 | 0 |
| | No | 18.2 | Yes | 20.2 | -2 |
| Above (Sea Level) | No | 16.2 | No | 16.2 | 0 |
| | Yes | 18.2 | No | 16.2 | 2 |
| | Yes | 18.2 | Yes | 18.2 | 0 |
| | No | 16.2 | Yes | 18.2 | -2 |
| Below (Sea Level) | No | 20.2 | No | 20.2 | 0 |
| | Yes | 22.2 | No | 20.2 | 2 |
| | Yes | 22.2 | Yes | 22.2 | 0 |
| | No | 20.2 | Yes | 22.2 | -2 |

SYSTEM AND METHOD FOR DETECTING ABNORMAL MEDICAMENT PUMP FLUID PRESSURE

BACKGROUND OF THE INVENTION

1. Field of the Invention

This invention relates to detecting abnormal pressure conditions upstream and downstream of a medicament pump having a pressurized source of fluid. More particularly, this invention is capable of indicating abnormal pressure conditions including: source overpressurization upstream of the pump and occlusion of the outlet tube downstream from the pump.

2. Description of Related Art

Medicament pumps, such as, the peristaltic pump disclosed in commonly assigned U.S. Pat. No. 4,576,556, which is incorporated herein by reference, are well known in the prior art and have wide application in the medical field. A typical application for such a pump is implanting the pump within a patient's body for treating a neurodegenerative disease or trauma, as is disclosed in commonly assigned U.S. Pat. No. 5,711,316, which is incorporated herein by reference. Other applications are also well known. The term "medicament pump" as used herein, refers to any device for delivering medicaments and having a pressurized reservoir, including, but not limited to, bladder pumps, accumulator pumps, fixed-rate bellows pumps, and the like.

Such a medicament pump will typically be coupled to a pressurized fluid source via an inlet tube and will typically administer medication or another fluid via a catheter coupled to the pump outlet via a pump outlet tube. A shortcoming of such pumps is their inability to detect, and provide an indication of, abnormal pressure conditions upstream and downstream of the pump. For instance, neither abnormally high upstream pressure, which could indicate reservoir overpressurization during reservoir refilling, nor abnormally high downstream pressure, which could indicate catheter occlusion, are detected by known prior art pumps having pressurized sources.

As certain therapies, which use a medicament pump, progress beyond treatment for pain and spasticity, immediate detection of potential catheter occlusion states, which could prevent drug delivery, is desirable. This is especially desirable for therapies which do not provide an immediate feedback as a clinical sign that interruption in therapy has occurred, for instance, therapies for Amyotrophic Lateral Sclerosis, Parkinson's Disease, and Alzheimer's Disease.

In addition, while the pressurized source of medication is being refilled, overfilling can cause source overpressurization, which can cause a pump to malfunction and could produce catastrophic results. Known prior art medicament pumps that have pressurized sources typically use a shut-off valve to mechanically close during the refill process to prevent reservoir overpressurization. Such mechanical valves tend to require close tolerances in order to optimize both reservoir volume and overpressurization protection, thereby undesirably increasing the complexity of fabrication of such reservoirs. In addition, such mechanical shut-off valves do not provide any indication that the source has been overfilled, or that the source is overpressurized.

The prior art fails to address these problems. For instance, U.S. Pat. No. 4,468,219 issued to George et al. ('219 patent) discloses a pump flow rate compensation system that speeds up a peristaltic pump motor in response to sensing that a transition from positive pump inlet pressure to a negative pump inlet pressure has occurred. The '219 patent does not disclose monitoring the downstream pressure, detection of abnormally high upstream or downstream pressures, or detection of an abnormal difference between downstream and upstream pressures.

U.S. Pat. No. 4,690,673 issued to Bloomquist ("'673 patent") discloses a dual mode intravenous infusion device with a distal sensor. The dual modes are: controller and pump. The controller does not contribute to the downstream fluid pressure. In the pumping mode, an alarm condition is triggered and the pump ceases operation upon detection of the downstream fluid pressure exceeding a threshold. In the controller mode, fluid pressure downstream is less than fluid pressure upstream under normal operating conditions. The device disclosed in the '673 patent triggers an alarm when the differential between the fluid pressure downstream from the controller and the fluid pressure upstream from the controller is a null. In other words, the '673 triggers an alarm when the downstream pressure increases up to, and equals, the upstream pressure. The '673 patent does not address the issue of detecting overpressurization of a fluid source. Therefore, the '673 patent does not disclose detection of abnormally high upstream pressure, with or without detection of abnormally high downstream pressure. The '673 patent also does not disclose detection of a condition in which the difference between the upstream and downstream pressures is outside a predetermined range of acceptable values.

Accordingly, there is a need in the prior art for a system and method that will detect abnormal pressure upstream, downstream, and differentially and, upon detection of such an abnormal pressure, will provide an indication of the abnormal pressure, such as by activating an alarm.

SUMMARY OF THE INVENTION

In one embodiment, this invention includes a system for providing an indication of an abnormal fluid pressure upstream of a medicament pump. The system includes: a pressurized source of fluid coupled to the pump inlet via a pump inlet tube; a pump inlet pressure sensor for sensing fluid pressure upstream from the pump; and an abnormal inlet pressure alarm coupled and responsive to the pump inlet pressure sensor. The inlet pressure sensor may be a strain gauge attached to, or incorporated into, the wall of the pump inlet tube.

The system is also capable of providing an indication of an abnormal fluid pressure downstream of the medicament pump. The system may further include: a pump outlet pressure sensor for sensing fluid pressure downstream from the pump; and an abnormal outlet pressure alarm coupled and responsive to the pump outlet pressure sensor. The outlet pressure sensor may be a strain gauge attached to, or incorporated into, the wall of the pump outlet tube.

In addition to monitoring the inlet, or upstream, and the outlet, or downstream, pressures individually, the system includes means for calculating the difference between the upstream and downstream pressures and means for indicating that the calculated difference is outside a predetermined range of acceptable difference pressure values. The components of this system may be adapted to be implanted within a person's body.

In another embodiment, this invention also includes a method of indicating abnormal fluid pressure upstream of a medicament pump. The method includes the steps of: monitoring the fluid pressure upstream of the pump; and activating an alarm based upon the monitored upstream fluid pressure being outside a predetermined acceptable range of values. This invention further includes a method for indicating abnormal fluid pressure downstream from the medicament pump. This method further includes the steps of: monitoring the fluid pressure downstream from the pump; and activating an abnormal outlet pressure alarm based upon the monitored downstream fluid pressure being outside a predetermined range of acceptable values. Additional steps include: calculating a difference between the upstream pressure and the downstream pressure; and activating an abnormal difference pressure alarm upon the calculated difference pressure being outside a predetermined acceptable range of values.

Also included is a method of indicating abnormal fluid pressure upstream and/or downstream of a peristaltic pump including the following steps: monitoring the fluid pressure upstream of the pump; monitoring the fluid pressure downstream from the pump; calculating a difference between the upstream pressure and the downstream pressure; and activating an abnormal difference pressure alarm upon the calculated difference pressure being outside a predetermined acceptable range of difference pressure values. Additional steps could include: activating an abnormal inlet pressure alarm based upon the monitored upstream fluid pressure being outside a predetermined acceptable range of inlet pressure values; and activating an abnormal outlet pressure alarm based upon the monitored downstream fluid pressure being outside a predetermined acceptable range of outlet values.

In a further embodiment, this invention comprises a medicament pump having a computer-readable medium, such as a random access memory, having computer-executable instructions for processing and providing signals. The computer-executable instructions and signals achieve essentially the same functionality as described above with respect to the method steps.

Each of these embodiments may be used separately or together in various combinations and permutations.

BRIEF DESCRIPTION OF THE DRAWINGS

FIG. 5 is a table showing exemplary representations of normal and abnormal pressure conditions monitored at a pump inlet and outlet.

FIG. 6 is an exemplary overpressurization truth table showing that the use of differential pressure values alone can be insufficient for distinguishing between normal pressure conditions and overpressurization at both the inlet and outlet simultaneously.

DESCRIPTION OF THE PREFERRED EMBODIMENTS

Figure 1:
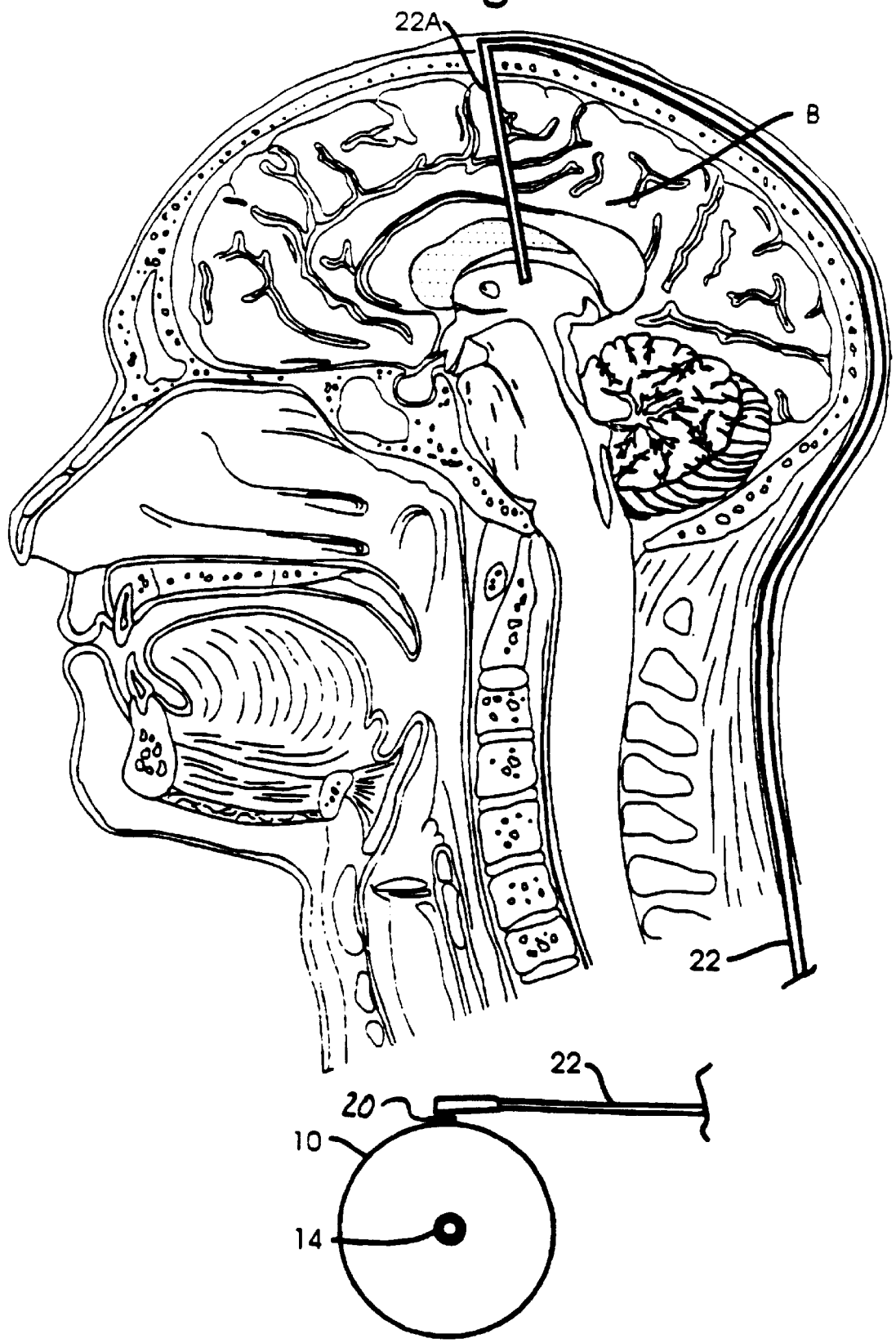
FIG. 1 is a diagrammatic illustration of a medicament pump coupled to a catheter that is implanted in the brain of a patient.

Referring to FIG. 1, a medicament pump 10 may be implanted below the skin of a patient. The device has a port 14 into which a hypodermic needle can be inserted through the skin to inject a quantity of a liquid agent, such as a medication or drug. The liquid agent is delivered from device 10 through a catheter port 20 into a catheter 22. Catheter 22 may be positioned to deliver the agent to specific infusion sites in brain (B).

Figure 2:
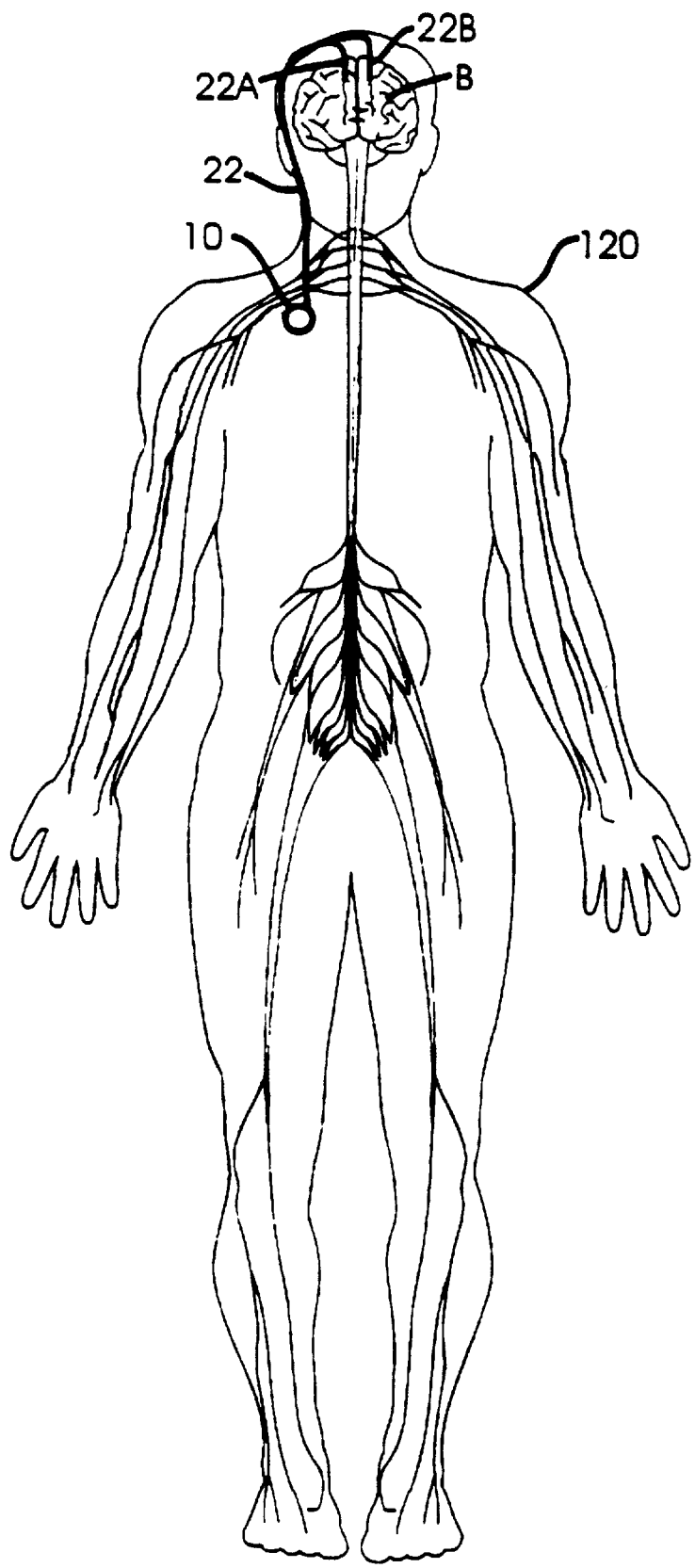
FIG. 2 is a diagrammatic illustration of a portion of the nervous system of a human body in which a medicament pump and catheter have been implanted.

Referring to FIG. 2, device 10 is implanted to a human body 120 in the location shown. Alternatively, device 10 may be implanted in the abdomen. Catheter 22 may be divided into twin tubes 22A and 22B that are implanted into the brain bilaterally. Alternatively, tube 22B may be supplied with medication from a separate catheter and pump.

Figure 3:
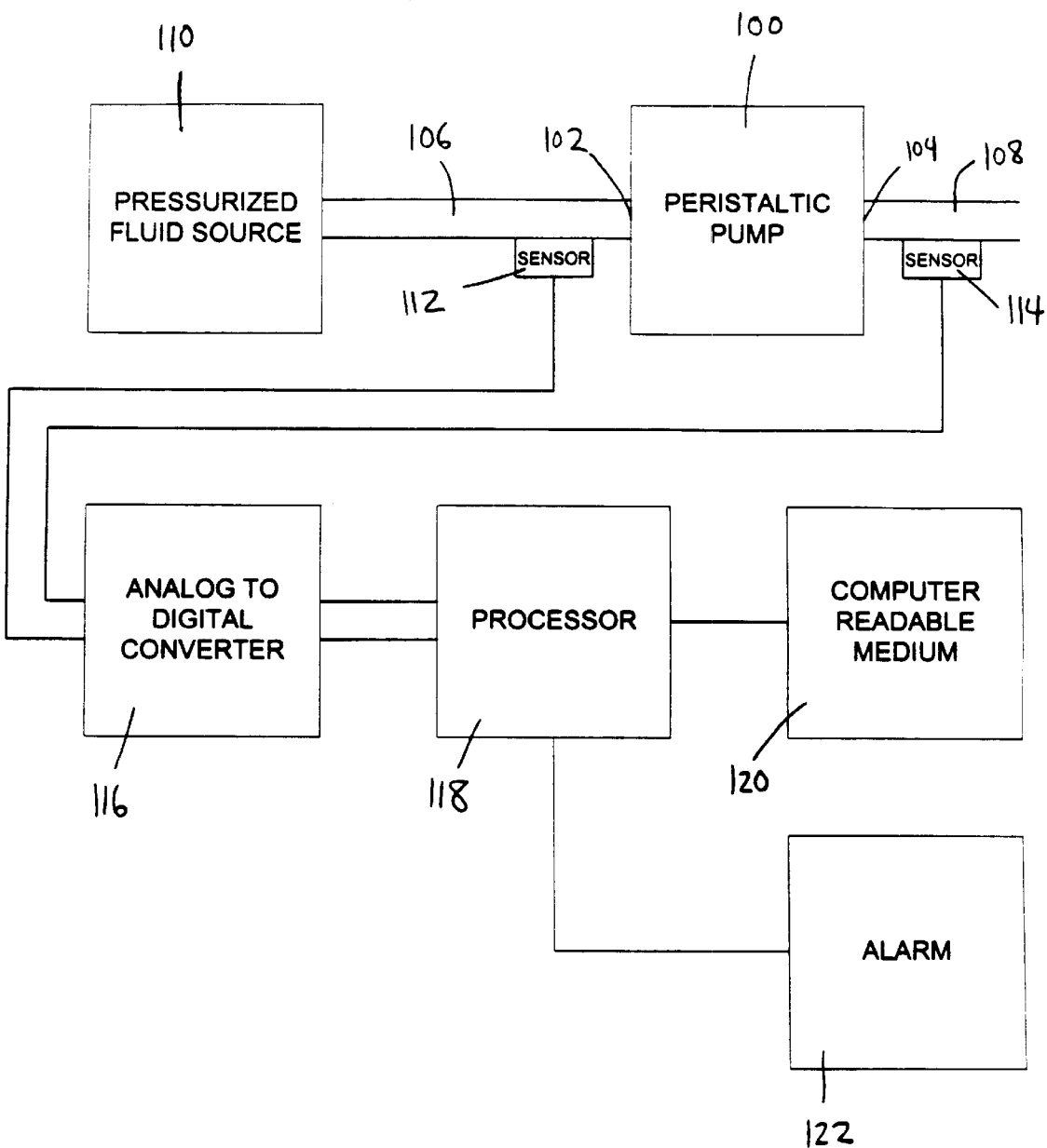
FIG. 3 is a simplified block diagram of an exemplary system according to the principles of this invention.

Referring to FIG. 3, a system according to the principles of this invention is shown schematically. The system in FIG. 3, includes a medicament pump, such as peristaltic pump 100, which could be a Synchromed® Infusion pump available from Medtronic Incorporated of Minneapolis, Minn. Pump 100 has an inlet 102 and an outlet 104. A first end of pump inlet tube 106 is coupled to pump inlet 102, and pump outlet tube 108 is coupled to pump outlet 104 in a conventional manner. Similarly, a second end of pump inlet tube 106 is coupled to pressurized fluid source 110 in a conventional manner.

Inlet or upstream fluid pressure sensor 112 may be a force transducer attached to, or incorporated into, the tubing wall of pump inlet tube 106 for monitoring fluid pressure upstream of pump 100 based on the amount of deformation of the wall of pump inlet tube 106. Similarly, outlet or downstream fluid pressure sensor 114 may be a force transducer attached or incorporated into the tubing wall of pump outlet tube 108 for monitoring fluid pressure downstream from pump 100 in a manner similar to sensor 112. Sensors 112 and 114 could be commercially available strain gauges. Other suitable force transducer arrangements could also be used.

Sensors 112 and 114 may be electrically coupled to processor 118 through analog to digital converter 116, as shown in FIG. 3. Sensors 112 and 114 could also be coupled to processor 118 in other suitable ways. Processor 118 is coupled to computer readable medium 120, which could be, for instance, a random access memory containing computer executable instructions. Processor 118 is coupled to alarm 122.

All of the components depicted in FIG. 3 could be implantable within a person's body, as disclosed in commonly assigned U.S. Pat. No. 4,692,147, which is incorporated herein by reference. Alarm 122 could be located outside the person's body. In such a scenario, alarm 122 could be a video display, an audio alarm, or any other suitable means for alerting the patient and/or one or more health care professionals that an abnormal pressure condition has been detected.

Figure 4:
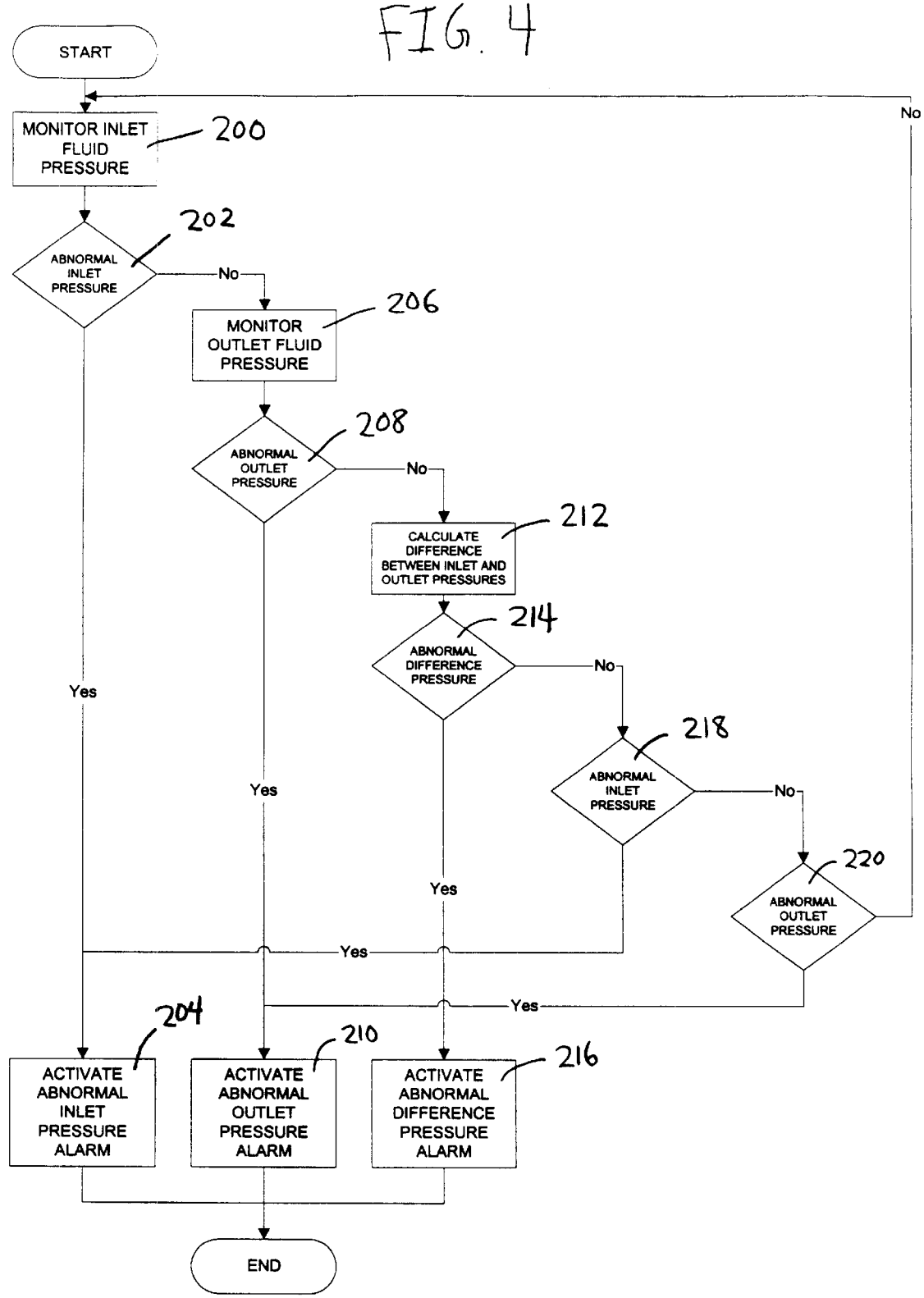
FIG. 4 is a simplified flowchart depicting exemplary steps for indicating detection of abnormal upstream fluid pressure, abnormal downstream fluid pressure, and an abnormal difference between the upstream and downstream pressures.

Referring to FIG. 4, exemplary steps in accordance with the principles of this invention are depicted. Inlet fluid pressure is monitored by upstream sensor 112 (FIG. 3), for instance, as depicted at 200. A determination is then made as to whether the monitored inlet fluid pressure is outside a predetermined range of acceptable inlet fluid pressure values, as depicted at 202. Inlet pressure sensor 112 could be calibrated to the acceptable range of inlet pressure values using a calibration technique in which a strain gauge, which is attached to the pump inlet tubing wall, produces a particular range of voltages corresponding to an acceptable amount of deformation of the wall of the inlet tubing, which range of voltages corresponds to an acceptable range of inlet fluid pressure values. Other suitable calibration techniques could also be used.

If the monitored inlet fluid pressure is outside a first acceptable range of inlet pressures, an abnormal inlet pressure alarm could be activated, as depicted at 204. If the abnormal inlet fluid pressure exceeds the predetermined acceptable range of values, the alarm could be activated so that the alarm indicates that reservoir or fluid source 110 (FIG. 3) is overpressurized. In this specification and the appended claims, activation of an alarm could include, but is not limited to, providing an alarm code, textual message, audible warning, and the like.

If the inlet fluid pressure is within the first predetermined range of acceptable values, the fluid pressure downstream of pump 100 is monitored, for instance, by sensor 114, as depicted in FIG. 4 at 206. A determination is then made as to whether the monitored outlet fluid pressure is outside the first predetermined range of acceptable outlet fluid pressure values, as depicted at 208. Outlet pressure sensor 114 could be calibrated in a manner similar to sensor 112 discussed above and could depend upon the particular intended route of administration for the indicated therapy, such as intrathecal, intra-arterial, intravenous, intra-cerebral ventricular or intrastitial.

If the monitored outlet fluid pressure is outside the first predetermined acceptable range of outlet pressure values, an abnormal outlet pressure alarm could be activated, as depicted at 210. If the abnormal outlet fluid pressure exceeds the first predetermined acceptable range of values, the alarm could be activated so that the alarm indicates that an occlusion has been detected downstream of pump 100.

If the inlet and outlet fluid pressures are both within their respective first predetermined range of acceptable values, the difference between the upstream and downstream fluid pressures is calculated, as depicted at 212. A determination is then made as to whether the difference between the monitored inlet fluid pressure and the monitored outlet fluid pressure is outside of a predetermined range of acceptable differential fluid pressure values, as depicted at 214. Differential pressure calculations can be calibrated in a manner similar to calibration of outlet pressure sensor 114 and inlet sensor 112 discussed above.

If the calculated difference between the monitored inlet fluid pressure and the monitored outlet fluid pressure is outside the acceptable range of differential pressures, an abnormal difference pressure alarm could be activated, as depicted at 216. If the abnormal difference fluid pressure exceeds the predetermined acceptable range of values, the alarm could be activated so that the alarm indicates that the source is overpressurized. If the abnormal difference fluid pressure is less than the predetermined acceptable range of values, the alarm could be activated so that the alarm indicates a likely catheter occlusion state or a likely source underpressurization state, or both, depending upon the measured inlet and outlet pressures. For instance, suppose the range of pressures measurable by the inlet sensor 112 and outlet sensor 114 were represented in computer readable medium 120 as numbers between 0 and 10. A table containing values such as those in FIG. 5 could be used to recognize various upstream and/or downstream pressure conditions, such as, potential source overpressurization and/or potential downstream catheter occlusion states. Suppose the first predetermined range of acceptable inlet pressure values is represented in the range of 6.0 to 8.0, inclusive, the first predetermined range of acceptable outlet pressure values is represented in the range of 2.0 to 4.0, inclusive, and the predetermined range of acceptable difference pressure values is represented from 3.0 to 5.0, inclusive. These simplified values are presented as examples and are not intended to limit this invention in any manner.

Referring to FIG. 5, scenarios 1 and 2 depict exemplary potential upstream/source overpressurization and underpressurization states, respectively, which are detectable solely by measurements made by inlet sensor 112. Similarly scenarios 3 and 4 depict exemplary potential downstream catheter overpressurization and underpressurization states, respectively, which are detectable solely by measurements made by outlet sensor 114. Scenarios 5–7 depict various exemplary normal pressure conditions measured at the inlet sensor and outlet sensors that also produce calculated difference pressure values within the predetermined acceptable range of difference pressure values, namely, greater than or equal to 3.0 and less than or equal to 5.0.

Scenario 8 depicts an exemplary condition in which the inlet and outlet pressures are within their normal ranges, but the calculated difference pressure representation of 2.0 is less than the predetermined acceptable range of difference pressure representations, namely, 3.0 to 5.0. Such a condition could be indicative of an occlusion downstream of the pump, which occlusion is not detectable using outlet pressure sensor 114 alone. Scenario 9 depicts an exemplary condition in which the inlet and outlet pressure are within their normal ranges, but the calculated difference pressure representation of 6.0 exceeds the predetermined acceptable range of difference pressure representations. Such a condition could be indicative of source overpressurization during refilling of pressurized source 110 and would not be detectable using inlet pressure sensor 112 alone.

Accordingly, by determining the difference between the inlet and outlet fluid pressures, potential downstream occlusion states and potential source overpressurization states can be detected, which states would not otherwise be detectable by monitoring only the downstream pressure, and/or the upstream pressure without determining their difference and whether that difference is within a predetermined range of acceptable values.

Referring to FIG. 6, an overpressurization state truth table contains similar data for conditions at sea level, above sea level, and below sea level. The assumptions are: Nominal pressurized fluid source pressure is 3.5 PSIG; overpressurization of the pressurized fluid source is 5.5 PSIG; nominal output back pressure, for instance, pressure inside a person's body, is 3.5 PSIG; catheter occlusion is 5.5 PSIG; above sea level is −2 PSIG; below sea level is 2 PSIG; and 0 PSIG equals 14.7 PSIA. At sea level, with neither the source nor the output overpressurized, the differential pressure is 0. With the source overpressurized and the output not overpressurized, the differential pressure is 2 PSID. With both the source and the output overpressurized, the differential pressure is 0. With only the output overpressurized, the differential is −2 PSID. Accordingly, differential pressure, by itself, is insufficient for distinguishing between the first state in which neither the source nor the output are overpressurized and the third state in which both the source and the output are overpressurized. Therefore, even when the differential pressure is within a normal range, it is preferable to verify that the inlet pressure and the outlet pressure are also within normal ranges.

Those skilled in the art, and others, will recognize that the preferred embodiments may be altered or amended without departing from the true spirit and scope of the invention, as defined by the accompanying claims and their equivalents. For instance, other suitable relationships between the ranges of normal inlet, outlet, and calculated difference pressure values could also be used, without departing from the scope of this invention.

I claim:

1. A system for providing an indication of an abnormal fluid pressure upstream or downstream or both upstream and downstream of a human-implantable medicament pump having a pressurized source of fluid operatively coupled to an inlet of the medicament pump, the system comprising:
   a pump inlet pressure sensor for sensing fluid pressure upstream from the pump;
   a pump outlet pressure sensor for sensing fluid pressure downstream from the pump; and
   a processor for calculating a difference between the pressure upstream of the pump and the pressure downstream of the pump and for providing an indication that the pressure upstream of the pump minus the pressure downstream of the pump is greater than a maximum-difference threshold.

2. The system as in claim 1 wherein the pump inlet pressure sensor comprises a strain gauge operatively attached to a wall of a pump inlet tube for monitoring fluid pressure in the pump inlet tube.

3. The system as in claim 1 wherein the pump inlet pressure sensor comprises a strain gauge incorporated into a wall of a pump inlet tube for monitoring fluid pressure in the pump inlet tube.

4. The system as in claim 1 wherein: the pump outlet pressure sensor comprises a strain gauge operatively attached to a wall of a pump outlet tube for detecting changes in fluid pressure downstream from the pump.

5. The system as in claim 1 wherein: the pump outlet pressure sensor comprises a strain gauge incorporated into a wall of a pump outlet tube for detecting changes in fluid pressure downstream from the pump.

6. A method of indicating abnormal fluid pressure upstream and/or downstream of a human-implantable medicament pump, the method comprising the steps of:
   monitoring the fluid pressure upstream of the pump;
   monitoring the fluid pressure downstream from the pump;
   calculating a difference between the upstream pressure and the downstream pressure; and
   activating an abnormal difference pressure alarm when the calculated difference pressure is greater than a maximum-difference threshold.

7. The method as in claim 6 further comprising the step of:
   activating an abnormal inlet pressure alarm when the monitored upstream fluid pressure is greater than a maximum-upstream-fluid-pressure threshold.

8. The method as in claim 7 further comprising the step of:
   activating an abnormal inlet pressure alarm when the monitored upstream fluid pressure is less than a minimum-upstream-fluid-pressure threshold.

9. A human-implantable medicament pump having a computer-readable medium, the computer-readable medium having computer-executable instructions for performing the steps recited in claim 6.

10. The medicament pump computer-readable medium as in claim 9 having computer-executable instructions for performing the steps recited in claim 7.

11. The medicament pump computer-readable medium as in claim 9 having computer-executable instructions for performing the steps recited in claim 8.

12. The system as in claim 1, the system further comprising:
    an abnormal inlet pressure alarm operatively coupled and responsive to the pump inlet pressure sensor for indicating abnormal fluid pressure upstream of the pump when the sensed fluid pressure upstream from the pump is greater than a maximum-upstream-fluid-pressure threshold.

13. The system as in claim 12, wherein the abnormal inlet pressure alarm indicates abnormal fluid pressure upstream of the pump when the sensed fluid pressure upstream from the pump is less than a minimum-upstream-fluid-pressure threshold.

14. The system as in claim 1, the system further comprising:
    an abnormal inlet pressure alarm operatively coupled and responsive to the pump inlet pressure sensor for indicating abnormal fluid pressure upstream of the pump when the sensed fluid pressure upstream from the pump is less than a minimum-upstream-fluid-pressure threshold.

15. The system as in claim 1, the system further comprising:
    an abnormal outlet pressure alarm operatively coupled and responsive to the pump outlet pressure sensor for indicating abnormal fluid pressure downstream from the pump when the sensed fluid pressure downstream from the pump is greater than a maximum-downstream-fluid-pressure threshold.

16. The system as in claim 15, wherein the abnormal outlet pressure alarm indicates abnormal fluid pressure downstream from the pump when the sensed fluid pressure downstream from the pump is less than a minimum-downstream-fluid-pressure threshold.

17. The system as in claim 1, the system further comprising:
    an abnormal outlet pressure alarm operatively coupled and responsive to the pump outlet pressure sensor for indicating abnormal fluid pressure downstream from the pump when the sensed fluid pressure downstream from the pump is less than a minimum-downstream-fluid-pressure threshold.

18. The system as in claim 1, wherein the processor provides an indication that the calculated difference is outside a predetermined range of acceptable difference pressure values when the pressure upstream of the pump minus the pressure downstream of the pump is less than a minimum-difference threshold.

19. The method as in claim 6 further comprising the step of:
    activating an abnormal inlet pressure alarm when the monitored upstream fluid pressure is less than a minimum-upstream-fluid-pressure threshold.

20. The method as in claim 6 further comprising the step of:
    activating an abnormal outlet pressure alarm when the monitored downstream fluid pressure is greater than a maximum-downstream-fluid-pressure threshold.

21. The method as in claim 20 further comprising the step of:
    activating the abnormal outlet pressure alarm when the monitored downstream fluid pressure is less than a minimum-downstream-fluid-pressure threshold.

22. The method as in claim 6 further comprising the step of:
    activating an abnormal outlet pressure alarm when the monitored downstream fluid pressure is less than a minimum-downstream-fluid-pressure threshold.

23. The method as in claim 6 further comprising the step of:
    activating the abnormal difference pressure alarm when the calculated difference pressure is less than a minimum-difference threshold.

24. The medicament pump computer-readable medium as in claim 9 having computer-executable instructions for performing the steps recited in claim 19.

25. The medicament pump computer-readable medium as in claim 9 having computer-executable instructions for performing the steps recited in claim 20.

26. The medicament pump computer-readable medium as in claim 25 having computer-executable instructions for performing the steps recited in claim 21.

27. The medicament pump computer-readable medium as in claim 9 having computer-executable instructions for performing the steps recited in claim 22.

28. The medicament pump computer-readable medium as in claim 9 having computer-executable instructions for performing the steps recited in claim 23.

* * * * *